United States Patent [19]

Hohensang

[11] Patent Number: 4,495,417

[45] Date of Patent: Jan. 22, 1985

[54] DEVICE FOR THE DETERMINATION OF THE SOOT CONTENT OF AN OIL SAMPLE

[75] Inventor: Lutz Hohensang, Hamburg, Fed. Rep. of Germany

[73] Assignee: Mobil Oil Corporation, New York, N.Y.

[21] Appl. No.: 435,787

[22] Filed: Oct. 21, 1982

[30] Foreign Application Priority Data

Nov. 7, 1981 [DE] Fed. Rep. of Germany ... 8132595[U]

[51] Int. Cl.³ .............................................. G01J 1/00
[52] U.S. Cl. ..................................... 250/343; 73/61.3
[58] Field of Search ............... 250/301, 308, 338 R, 250/339, 341, 343; 73/61.3, 64; 356/70, 440; 313/112

[56] References Cited

U.S. PATENT DOCUMENTS

| | | | |
|---|---|---|---|
| 3,049,964 | 8/1962 | Miller et al. | 356/70 |
| 3,526,127 | 9/1970 | Sarkis | 250/343 |
| 3,581,085 | 5/1971 | Barrett | 250/301 |
| 4,281,533 | 8/1981 | Eesley et al. | 73/61.3 |
| 4,345,202 | 8/1982 | Nagy et al. | 73/64 |

Primary Examiner—Janice A. Howell
Attorney, Agent, or Firm—Alexander J. McKillop; Michael G. Gilman; Howard M. Flournoy

[57] ABSTRACT

A device for the detection of soot content of an oil sample is provided comprising a source of infrared radiation, an oil-sample receptacle of infrared permeable material, an infrared detector and an independent power means.

7 Claims, 1 Drawing Figure

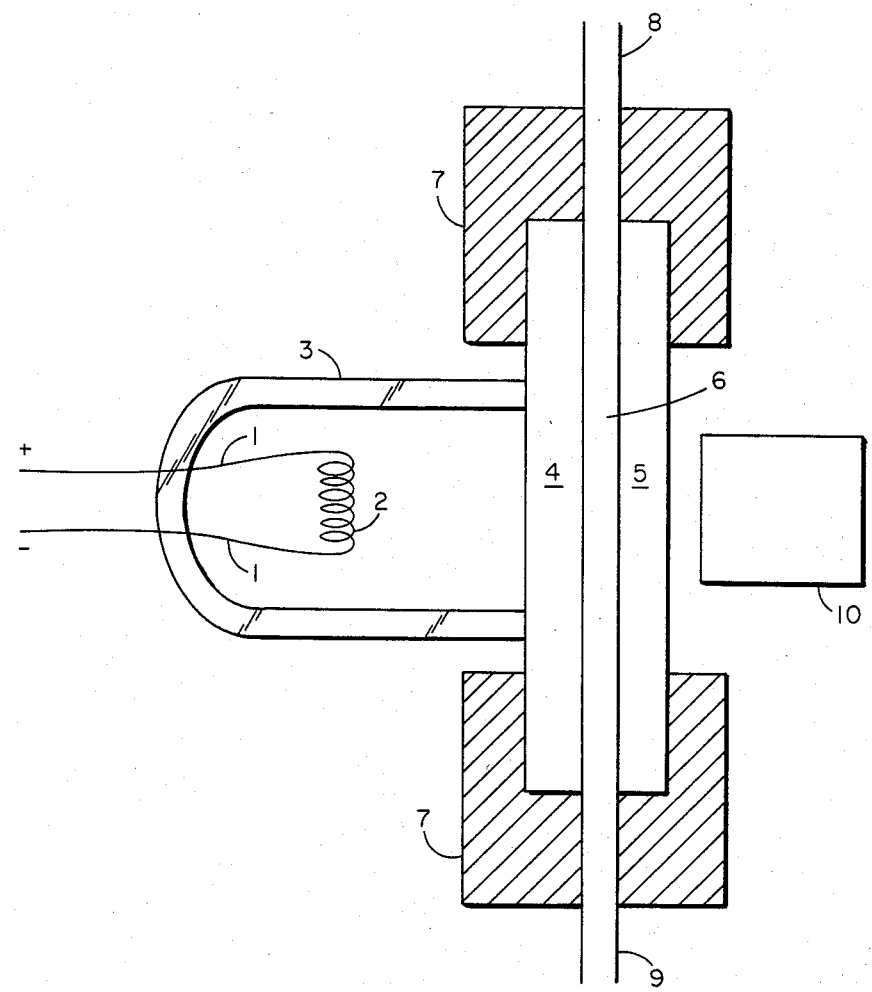

DEVICE FOR THE DETERMINATION OF THE SOOT CONTENT OF AN OIL SAMPLE

CROSS REFERENCE TO RELATED APPLICATIONS

This application is related to German Gebrauchmuster G No. 8132595.9, DEVICE FOR MONITORING THE CARBON CONTENT OF DIESEL ENGINE OILS, filed Nov. 7, 1981.

BACKGROUND OF THE INVENTION

1. Field of the Invention

This application is directed to and concerned with a method and means of determining the soot content of used oil. More specifically, this invention relates to engine oil analysis apparatus and to a system including an improved infrared analysis apparatus for analyzing the soot content of oil samples.

2. Discussion of Prior Art

An effective oil analysis program to determine soot content in the engine oil and, ultimately, the engine's condition and operation, has been a cherished goal for quite some time. The reason is to optimize oil life, optimize engine life, optimize filter life and minimize maintenance costs. An effective oil analysis can also be used to determine the causes of various engine problems which may be encountered and is therefore useful in diagnosing engine problems and trends. Engine malfunctions which are determined in the analysis can be corrected early through minor maintenance and with minimum cost before the malfunction gets progressively worse.

Soot plays a decisive role in the service life of oil and motors. A motor can hold only a certain amount of soot and if the oil change is not timely, the oil detergent additive, overloaded with soot, is deposited in the motor while it is not operating, and forms a gummy substance with the soot which no longer dissolves when the motor is reactivated. Under these conditions, damage to the motor appears within a relatively short time. The amount of soot produced depends on many factors, for example, motor type, manner of operation and motor setting.

For many years attempts have been made to make available to motor operators a measuring device which would make an easy yet reliable determination of the soot content possible and also permit an estimation of the length of oil service life still remaining. Such a device must be easy to handle by auto repair shops and construction site personnel and have independent power means. To the best of our knowledge all previous developments of devices of the aforementioned type have not, however, fulfilled these objectives. For example, see U.S. Pat. No. 3,619,072. It is believed, therefore, that no prior art apparatus for analyzing oil samples has the combination of ease of handling, independence of external energy source and efficiency geared for analysis of the subject important parameter (soot content) in a used oil sample as disclosed and claimed in the present invention.

SUMMARY OF THE INVENTION

This invention is directed to a device or apparatus for the determination of the soot of an oil sample comprising a source of infrared radiation, an oil-sample receptacle of infrared permeable material, an infrared detector and an independent external source of electrical power. Means are provided to secure short optical paths between the radiation source and the detector, so that the use of a radiator with a low power consumption is possible. Even a flashlight battery can be used as an external power source.

The infrared radiation detector which is placed on a side opposite to the oil-sample receptacle can be any suitable commercially available device which is attached with its absorption aperture to the side facing away from the radiation of the aperture of the oil-sample receptacle. See the FIGURE. This radiation detector can provide a reading of the soot content found in the sample, and on the other hand, can provide a reading in absorption coefficient units. However, it is possible in accordance with the invention, to get a reading concerning the utility or the non-utility of the oil being examined using a digital indicator by illuminating designated small lamps or the like.

Therefore, this application is directed to an apparatus and a method for determining the soot content of an oil sample comprising a source of infrared radiation, an oil-sample receptacle of infrared permeable material and an infrared detector and a power source, said apparatus having one side or an aperture in said side of the oil-sample receptacle form a part of the bulb of a small incandenscent lamp containing said source of infrared radiation and having the infrared detector placed on the side opposite the oil-sample receptacle.

DESCRIPTION OF THE DRAWING

The FIGURE is a schematic representation of a device according to the invention.

DESCRIPTION OF SPECIFIC EMBODIMENTS

A fundamental concept of the invention is, so to speak, the "melting together" of the bulb of a small incandescent lamp with the oil-sample receptacle. That is, either the side of the sample receptacle is a part of the bulb of the small incandescent lamp, or a part of the bulb of the small incandescent lamp is at the same time a side of the sample receptacle. In this way, short optical paths are secured between the radiation source and the detector enabling, as mentioned hereinabove, the use of low power sources such as flashlight batteries with the infrared radiator.

Referring to the FIGURE, coil supports are indicated by (1), between which there is a coil (2). The coil (2) is supplied with current through the wires so that it emits a specific infrared radiation. The coil (2) is surrounded by a bulb (3) which has a generally-known shape of a small, glass socket bulb. However, an infrared permeable part is attached to the side opposite the power supply which forms the other side (4) of a small receptacle (6). The other side also consists of an infrared permeable material so that the infrared radiation emanating from the coil (2) can reach the infrared detector (10). The distance between the side parts (4) and (5) is kept at an exact appropriate value by spacers which are not shown. Two identical mounting sections (7) are used for the passages (8) and (9) which are connected to the sample receptacle (6).

The special construction design of the hollow space or of the trial space (6) has an exactly defined dimension which impacts on the reading of the detector (10) in test or calibration procedures on the soot-containing oil samples. Further, a calculating device can be used which receives electrical signals from the detector (10)

and generates an output according to the magnitude of the signal, and which informs the service attendent that the oil being tested should no longer be used or can be further used. A reading from the measuring instrument can also be used to make an estimate of the remaining oil service life.

The procedure for operating the device in accordance with the invention is as follows. A detergent is introduced into the hollow space (6) through the oil inlet (8) in order to remove oil residues and the like from the hollow space (6). The oil to be tested is then introduced into the oil inlet (8) which accommodates a few milliliters of oil. The coil (2) is then connected to a power source which preferably is a battery of low voltage, for example, 6 or 8 volts, and may be built into the device. The infrared radiation emitted passes through the side (4) and through the oil sample and the side (5) to the detector (10), which gives a reading corresponding to the soot content of the oil sample being taken. Further, the device according to the invention may be constructed as a fully encapsulated unit in which only the oil inlet and the oil outflow are open to the outside. An on-off switch for the circuit of the coil is attached to the device and a reading is provided either in digital or analog form.

Any of a number of suitable substances may be used for the infrared permeable sides. Preferred are materials such as calcium fluoride. The infrared permeable sides may be attached in any convenient manner, for example, glued or cemented to the glass bulb of the small incandescent lamp.

The mounting parts (7) for the sample receptacle can be made of metal and so constructed that a subsequent change in the distance of the hollow space is precluded. The selection of the metal is not critical. Any suitable metal known to those with skill in the art can be so used.

Many infrared measurements in other fields can be easily and inexpensively carried out with the device described hereinabove. Also, since soot does not have well-defined absorption bands, but rather absorbs over a larger range of wave frequencies, gratings or prisms are not necessary for use in the instant device. As stated hereinabove, the principles of this invention are in no way limited to measurements of soot. For other applications however, a suitable filter must be placed in the path of the rays of the device, such as between the test tube and the receiver, which lets only the desired range of wave frequencies through and the layer thickness of the test tube must also be adjusted for each respective task.

For example, the apparatus as disclosed herein, can be adapted for measuring physical properties other than the soot content of oil samples by inserting at predetermined points in the path of the infrared radiation suitable filtering devices.

Although the present invention has been described with preferred embodiments, it is to be understood that modifications and variations may be restored to, without departing from the spirit and scope of this invention, as those skilled in the art will readily understand. Such modifications and variations are considered to be within the purview and scope of the appended claims.

I claim:

1. An apparatus for determining the soot content of an oil sample comprising a source of infrared radiation, an oil-sample receptacle of infrared permeable material and an infrared detector and a power source, said apparatus having one side or an aperture in said side of the oil-sample receptacle form a part of the bulb of a small incandescent lamp containing said source of infrared radiation and having the infrared detector placed on the side opposite the oil-sample receptacle.

2. The apparatus of claim 1 wherein the side or the aperture in the side of the oil-sample receptacle is made of calcium fluoride.

3. An apparatus in accordance with claims 1 or 2 wherein the oil-sample receptacle is a narrow test tube having a narrow, hollow space therein for sample material between the sides of the oil-sample receptacle.

4. The apparatus as defined in claim 3 wherein the hollow space provided for the oil-sample is connected to an inlet and an outlet duct.

5. The apparatus as defined in claim 1 wherein the power source is a flashlight battery of suitably low voltage.

6. An apparatus as defined in claim 1 adapted for measuring physical properties other than the soot content of oil samples characterized by inserting at predetermined points in the path of the infrared radiation suitable filtering devices.

7. A method for determining the soot content of an oil-sample comprising exposing said sample to a source of infrared radiation in a device consisting essentially of a source of infrared radiation, an oil-sample receptacle of infrared permeable material and an infrared detector and a power source, said apparatus having one side or an aperture in said side of the oil-sample receptacle form a part of the bulb of a small incandescent lamp containing said source of infrared radiation and having the infrared detector placed on the side opposite of the oil-sample receptacle.

* * * * *